United States Patent [19]

Sauerberg et al.

[11] Patent Number: 5,591,755
[45] Date of Patent: *Jan. 7, 1997

[54] PYRIDINYL THIADIAZOLYL COMPOUNDS FOR TREATING GLAUCOMA

[75] Inventors: Per Sauerberg, Valby; Preben H. Olesen, Copenhagen, both of Denmark

[73] Assignee: Novo Nordisk A/S, Bagsvaerd, Denmark

[ * ] Notice: The term of this patent shall not extend beyond the expiration date of Pat. No. 5,534,528.

[21] Appl. No.: 472,350

[22] Filed: Jun. 7, 1995

Related U.S. Application Data

[60] Continuation of Ser. No. 145,286, Oct. 29, 1993, abandoned, which is a division of Ser. No. 744,150, Aug. 13, 1991, Pat. No. 5,328,923.

[30] Foreign Application Priority Data

Aug. 21, 1990 [DK] Denmark ................................. 1984/90

[51] Int. Cl.$^6$ .......................... C07D 417/04; A61K 31/44
[52] U.S. Cl. ............................................. 514/342; 514/340
[58] Field of Search ................................. 546/276, 277; 514/340, 342

[56] References Cited

U.S. PATENT DOCUMENTS 4,837,241  6/1989  Jensen ..................................... 514/340
4,933,353  6/1990  Jenssen .................................... 514/340
5,017,618  12/1992  Border ..................................... 514/650

OTHER PUBLICATIONS

Tune et al. "Anticolinergic delirium caused by topical homatropine ophthalmologic solution" Index Medicus 330504 (1992).

Sugrue "The pharmacology of antiglaucoma drugs" Pharm. Ther. v. 43, pp. 91–138 (1989).

Bodor et al. "Improved delivery through biological membrane" J. Med. Chem. v. 31, p. 100–106 (1988).

Wilbraham et al. "Organic and biological chemistry" The Benjamin/Cummins Pub. pp. 266–269 (1985).

Sugrue "The Pharmacology of autiglaucoma" Pharma. Ther. 43 91–138 (1989) (reference pages not attached.).

*Primary Examiner*—Ceila Chang
*Attorney, Agent, or Firm*—Steve T. Zelson, Esq.; Elias J. Lambiris, Esq.

[57] ABSTRACT

The present invention relates to therapeutically active azacyclic compounds, a method of preparing the same and to pharmaceutical compositions comprising the compounds. The novel compounds are useful as stimulants of the cognitive function of the forebrain and hippocampus of mammals and especially in the treatment of Alzheimer's disease, severe painful conditions and glaucoma.

6 Claims, No Drawings

PYRIDINYL THIADIAZOLYL COMPOUNDS FOR TREATING GLAUCOMA

This application is a continuation of U.S. application Ser. No. 08/145,286 filed Oct. 29, 1993, now abandoned, which is a divisional of U.S. application Ser. No. 07/744,150 filed Aug. 13, 1991, now U.S. Pat. No. 5,328,923, the contents of which are incorporated herein by reference.

The present invention relates to therapeutically active azacyclic compounds, a method of preparing the same and to pharmaceutical compositions comprising the compounds. The novel compounds are useful as stimulants of the cognitive function of the forebrain and hippocampus of mammals and especially in the treatment of Alzheimer's disease.

Due to the in general improved health situation in the western world, elderly-related diseases are much more common now than in the past and are likely to be even more common in the future.

One of the elderly-related symptoms is a reduction of the cognitive functions. This symptom is especially pronounced in the patophysiological disease known as Alzheimer's disease. This disease is combined with, and also most likely caused by, a up to 90% degeneration of the muscarinic cholinergic neurons in nucleus basalis, which is part of substantia innominata. These neurons project to the prefrontal cortex and hippocampus and have a general stimulatory effect on the cognitive functions of the forebrain as well as of hippocampus, namely learning, association, consolidation, and recognition.

It is a characteristic of Alzheimer's disease that although the cholinergic neurons degenerate, then the postsynaptic muscarinic receptors in the forebrain and hippocampus still exist. Therefore muscarinic cholinergic antagonists are useful in the treatment of Alzheimer's disease and in improving the cognitive functions of elderly people.

It is well known that arecoline (methyl 1-methyl-1,2,5,6-tetrahydropyridine-3-carboxylate) is such a cholinergic agonist.

Arecoline however has a very short biological half life and a small separation between central and peripheral muscarinic effects. Furthermore arecoline is a rather toxic compound.

EP-A-0307142 discloses a class of thiadiazoles, substituted on one of the ring carbon atoms with a non-aromatic azacyclic or azabicyclic ring system, and substituted on the other ring carbon atom with a substituent of low lipophilicity, or a hydrocarbon substituent, which are muscarinic agonists and therefore useful in the treatment of neurological and mental illnesses and severe painful conditions.

It is an object of the invention to provide new muscarinic cholinergic compounds.

The novel compounds of the invention are heterocyclic compounds having the formula I

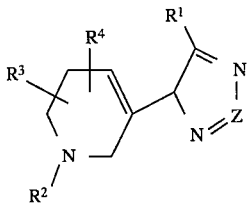

wherein Z is oxygen or sulphur;

$R^1$ is Y which represents H, halogen, —$CF_3$, —CN, —CHO, —OH, —$NH_2$, —$NO_2$, —CONH —$OR^5$, —$SR^5$, —$NHR^5$, —$NR^5$, —$R^6$, —$SOR^5$, —$SO_2R^5$—$COR^5$, —$CO_2R^5$, —$CONHR^5$, —$CONR^5R^6$, —CH=$NOR^5$, phenyl, phenoxy, benzoyl, benzyl or benzyloxycarbonyl groups optionally substituted with halogen, —CN, $C_{1-4}$-alkyl or $C_{1-4}$-alkoxy, or a 5 or 6 membered heterocyclic group containing one to three N, O or S atom(s) or a combination thereof being saturated, partly saturated or aromatic, $R^5$ substituted with Y, or $ZR^5$ substituted with Y, wherein $R^5$ and $R^6$ independently are straight or branched $C_{1-15}$-alkyl, straight or branched $C_{2-15}$-alkenyl, straight or branched $C_{2-15}$-alkynyl, phenyl, phenoxy, benzoyl, benzyl or benzyloxycarbonyl Groups optionally substituted with halogen, —CN, $C_{1-4}$-alkyl or $C_{1-4}$-alkoxy, or a 5 or 6 membered heterocyclic group containing one to three N, O or S atom(s) or a combination thereof being saturated, partly saturated or aromatic, and $R^2$ is H, straight or branched $C_{1-5}$-alkyl, straight or branched $C_{2-5}$-alkenyl, or straight or branched $C_{2-5}$-alkynyl and $R^3$ and $R^4$ which may be present in any position independently are H, straight or branched $C_{1-5}$-alkyl, straight or branched $C_{2-5}$-alkenyl, straight or branched $C_{2-5}$-alkynyl, straight or branched $C_{1-5}$-alkoxy, halogen, —OH, —$NH_2$, with the proviso that only one of $R^3$ or $R^4$ is H or a salt thereof with a pharmaceutically-acceptable acid.

Examples of such salts include inorganic and organic acid addition salts such as hydrochloride, hydrobromide, sulphate, phosphate, acetate, fumarate, maleate, citrate, lactate, tartrate, oxalate, or similar pharmaceutically-acceptable inorganic or organic acid addition salt.

The compounds of this invention are also useful analgesic agents and therefore useful in the treatment of severe painful conditions.

Furthermore, the compounds of this invention are useful in the treatment of glaucoma.

The invention also relates to a method of preparing the above mentioned compounds, which comprises alkylating a compound having the formula II

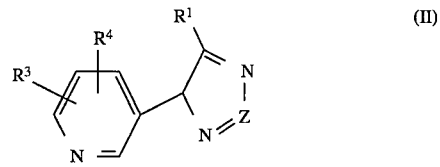

wherein Z, $R^1$ $R^3$ and $R^4$ have the meanings defined above, with an alkyl halide and reducing the compound thus formed with hydride ions to form a compound having the formula I

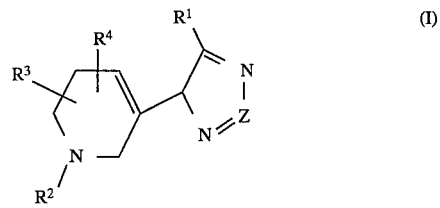

wherein Z, $R^1$, $R^2$, $R^3$ and $R^4$ have the meanings defined above.

The pharmacological properties of the compounds of the invention can be illustrated by determining their capability to inhibit the specific binding of $^3$H-Oxotremorine-M ($^3$H-Oxo). Birdsdall N. J. M., Hulme E. C., and Burgen A. S. V. (1980). "The Character of Muscarinic Receptors in Different Regions of the Rat Brain". Proc. Roy. Soc. London (Series B) 207,1. $^3$H-Oxo labels muscarinic receptor in the CNS (with a preference for agonist domaines of the receptors). Three different sites are labelled by $^3$H-Oxo. These sites have affinity of 1.8, 20 and 3000 nM, respectively. Using the present experimental conditions only the high and medium affinity sites are determined.

The inhibitory effects of compounds on $^3$H-Oxo binding reflects the affinity for muscarinic acetylcholine receptors.

All preparations are performed at 0°–4° C. unless otherwise indicated. Fresh cortex (0.1–1 g) from male Wistar rats (150–250 g) is homogenized for 5–10 s in 10 ml 20 mM Hepes pH: 7.4, with an Ultra-Turrax homogenizer. The homogenizer is rinsed with 10 ml of buffer and the combined suspension centrifuged for 15 min at 40,000×g. The pellet is washed three times with buffer. In each step the pellet is homogenized as before in 2×10 ml of buffer and centrifuged for 10 min at 40,000×g.

The final pellet is homogenized in 20 mM Hepes pH: 7.4 (100 ml per g of original tissue) and used for binding assay. Aliquots of 0.5 ml is added 25 µl of test solution and 25 µl of 3H-Oxotremorine (1.0 nM, final concentration) mixed and incubated for 30 min at 25° C. Non-specific binding is determined in triplicate using arecoline (1 µg/ml, final concentration) as the test substance. After incubation samples are added 5 ml of ice-cold buffer and poured directly onto Whatman GF/C glass fiber filters under suction and immediately washed 2 times with 5 ml of ice-cold buffer. The amount of radioactivity on the filters are determined by conventional liquid scintillation counting. Specific binding is total binding minus non specific binding.

Test substances are dissolved in 10 ml water (if necessary heated on a steambath for less than 5 minutes) at a concentration of 2.2 mg/ml. 25–75% inhibition of specific binding must be obtained before calculation of $IC_{50}$.

The test value will be given as $IC_{50}$ (the concentration (ng/ml) of the test substance which inhibits the specific binding of $^3$H-Oxo by 50%).

$$IC_{50} = \text{(applied test substance concentration)} \times \frac{1}{\left(\frac{C_o}{C_x} - 1\right)} \text{ ng/ml}$$

where $C_o$ is specific binding in control assays and $C_x$ is the specific binding in the test assay. (The calculations assume normal mass-action kinetics).

Test results obtained by testing some compounds of the present invention will appear from the following table 1.

TABLE 1

| Compound No. | Inhibition in vitro OXO BINDING (ng/ml) |
|---|---|
| 1 | 108 |
| 2 | 18 |
| 3 | 4.5 |
| 4 | 2.0 |
| 5 | 1.9 |
| 6 | 2.4 |
| 7 | 3.3 |
| 8 | 0.69 |

The compounds of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective muscarinic cholinergic agonistic amount of the active ingredient commensurate with the intended daily dosage range to be employed. Tablets containing ten (10) milligrams of the active ingredient or, more broadly, one (1) to hundred (100) milligrams, per tablet, are accordingly suitable representative unit dosage forms.

The compounds of this invention can thus be used for the formulation of pharmaceutical preparations, e.g. for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethyl-cellulose and polyvinylpyrrolidone.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are convenient unit dosage forms.

Tablets, dragees, or capsules having talc and/or a carbohydrate carrier or binder or the like, the carrier preferably being lactose and/or corn starch and/or potato starch, are particularly suitable for oral application. A syrup, elixir of the like can be used in cases where a sweetened vehicle can be employed.

Generally, the compounds of this invention are dispensed in unit form comprising 1–100 mg in a pharmaceutically acceptable carrier per unit dosage.

The dosage of the compounds according to this invention is 1–100 mg/day, preferably 10–70 mg/day, when administered to patients, e.g. humans, as a drug.

A typical tablet which may be prepared by conventional tabletting techniques contains:

| Active compound | 5.0 mg |
| Lactosum | 67.8 mg Ph.Eur. |
| Avicel ® | 31.4 mg |
| Amberlite ® | 1.0 mg |
| Magnesii stearas | 0.25 mg Ph.Eur. |

Due to the high muscarinic cholinergic receptor agonistic activity, the compounds of the invention are extremely useful in the treatment symptoms related to a reduction of the cognitive functions of the brain of mammals, when administered in an amount effective for stimulating the cognitive functions of the forebrain and hippocampus. The important stimulating activity of the compounds of the invention includes both activity against the patophysiological disease, Alzheimer's disease as well as against normal degeneration of brain function. The compounds of the invention may accordingly be administered to a subject, e.g., a living animal body, including a human, in need of stimulation of the cognitive functions of the forebrain and hippocampus, and if desired in the form of a pharmaceutically-acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective forebrain and hippocampus stimulating amount, and in any event an amount which is effective for improving the cognitive function of mammals due to their muscarinic cholinergic receptor agonistic activity. Suitable dosage ranges are 1–100 milligrams daily, 10–100 milligrams daily, and especially 30–70 milligrams daily, depending as usual upon the exact mode of administration, form in which administered, the indication toward which the administration is directed, the subject involved and the body weight of the subject involved, and the preference and experience of the physician or veterinarian in charge.

The invention will now be described in further detail with reference to the following examples:

EXAMPLE 1

A.
4-Methyl-1-(phenoxycarbonyl)-1,4-dihydropyridine

In a dry 500 ml three neck flask under nitrogen, a solution of cuprous iodide (0.28 g, 1.5 mmol) and dimethyl sulfide (8 ml) in 30 ml of dry THF was stirred at room temperature for 10 minutes. Pyridine (2.43 ml, 30 mmol) in 120 ml of dry THF was added to the reaction, then cooled to −25° C. Phenylchloroformate (3.9 ml, 30 mmol) in 10 ml dry THF was added to the reaction via an addition funnel (a thick brown precipitate formed immediately upon addition). The mixture was stirred for 15 minutes. Methyl magnesium chloride (10 ml, 30 mmol) was added to the mixture via syringe whereupon the brown precipitate dissolved. The reaction was stirred at −25° C. for 20 minutes then stirred at room temperature for 20 minutes. 20% $NH_4Cl_{(aq)}$ (70 ml) was added to the reaction. The mixture was then extracted with 150 ml diethyl ether. The organic extract was then washed with 40 ml portions of 20% $NH_4Cl_{(aq)}/NH_4OH$ (1:1), water, 10% $HCl_{(aq)}$, water, and brine. The organic layer was then dried over $NaCl/Na_2SO_4$, filtered, and concentrated to yield 5.9 g of a yellow oil. Kugelrohr distillation (bp. 150°–170° C., 1 mmHg) to yield 4.9 g (77%) of the desired compound (A).

B. 3-Formyl-4-methyl-1-(phenoxycarbonyl)-1,4-dihydropyridine

To a dry 50 ml flask under nitrogen, DMF (7.44 ml, 97 mmol) in 10 ml of dichloromethane was cooled to 0° C. Phosphorus oxychloride (4.5 ml, 48 mmol) was slowly added to the solution. The solution was stirred at room temperature for 30 minutes. (A) (4.7 g, 22 mmol) in 40 ml of dichloromethane was stirred in a 100 ml two neck flask under nitrogen at 0° C. The DMF/Phosphorus oxychloride solution was transferred to an addition funnel via cannula then slowly added to the (A)/dichloromethane solution. The ice bath was then removed, and the reaction was stirred at room temperature for 20 hours. The reaction was cooled to 0° C. whereupon a solution of potassium acetate (15 g) in 50 ml of water was carefully added via the addition funnel. The mixture was then allowed to reflux for 20 minutes. The methylene chloride layer was separated then extracted once more with 100 ml methylene chloride. The organic phases were combined then washed with 40 ml portions of water, $K_2CO_3$(aq), water and brine, then dried over $NaCl/Na_2SO_4$.

The organics were concentrated on a rotary evaporator to yield 4 g of a brown oil. Purified by flash chromatography over silica gel eluting with ethyl acetate/hexane. Yield 2.0 g (37%) of the desired compound (B).

C. 4-Methyl-3-pyridinecarboxaldehyde

Methanol (85 ml), triethylamine (1.4 g), and (B) (5.0 g, 20.6 mmol) were placed in a 250 ml flask over nitrogen. The solution was refluxed for 3 hours. The reaction was then concentrated and 5% Pd/C (0.5 g) and toluene (85 ml) were added to the flask. This mixture was refluxed for 2 hours, then cooled to room temperature. The 5% Pd/C was removed by filtration and the filtrate was concentrated.

The resulting oil was purified by flash chromatography over silica gel eluting with ethyl acetate/hexane. The yield of (C) was 1.3 g (47%).

D.
Alpha-amino-alpha(3-(4-methylpyridyl)acetonitrile

Dissolved potassium cyanide (7.3 g, 112.6 mmol) and ammonium chloride (6.0 g, 112.6 mmol) in water (150 ml) in a 250 ml flask under nitrogen. (C) (10.9 g, 90.1 mmol) was added to the reaction which was stirred at room temperature overnight. The reaction mixture was extracted with ethyl acetate (3×300 ml). The organic extracts were combined, dried over $NaCl/Na_2SO_4$, then concentrated to yield 11 g of a brown oil (D). Used directly in the next step.

E.
3-(4-Chloro-1,2,5-thiadiazol-3-yl)-4-methylpyridine.

Sulfurmonochloride (73.5 mmol, 5.9 ml) in DMF (90 ml) was placed in a 250 ml flask under nitrogen and cooled to −25° C. (D) (3.6 g, 24.5 mmol) in DMF (10 ml) was added to the reaction via an additional funnel. The reaction was allowed to stir overnight. After warming to room temperature, water (30 ml) and diethyl ether (60 ml) were added to the reaction and the ether layer was separated, then discarded. The reaction was then basified with 50% NaOH $_{(aq)}$, then extracted with diethyl ether (4×90 ml). The organic extracts were combined, dried over $NaCl/NaSO_4$, and concentrated to yield a brown oil. The oil was purified by flash chromatography over 100 g silica gel, eluting with 0.05%$NH_4OH$/0.5% ethanol in chlorofom. Yield of (E) was 2 g (38%).

F.
3-(4-Methoxy-1,2,5-thiadiazol-3-yl)-4-methylpyridine

A solution of sodium (0.32 g, 14 mmol) in methanol (10 ml) was prepared in a 25 ml flask under nitrogen. (E) (0.6 g, 2.8 mmol) was added to the reaction and was heated at 50° C. for 3 hours, then stirred overnight at room temperature. Concentrated on the rotary evaporator then dissolved the resulting solid in 1N $HCl_{(aq)}$ and washed with diethyl ether. The aqueous layer was basified with 5N $NaOH_{(aq)}$, then extracted with methylene chloride (4 ×50 ml). The combined organic extracts were dried over $NaCl/Na_2SO_4$ and concentrated to yield 344 ml of an oil (F) (60%).

G.
3-(4-Methoxy-1,2,5-thiadiazol-3-yl)-4-methylpyridinium iodide

A mixture of (f) (335 mg, 1.6 mmol), iodomethane (1.14 g, 8.0 mmol), and acetone (100 ml) was stirred in a 250 ml flask under nitrogen overnight at room temperature. Concentrated the reaction on the rotary evaporator to yield 500 mg of a yellow solid (G). Used directly in next step.

H.
1,2,5,6-Tetrahydro-3-(4-methoxy-1,2,5-thiadiazol-3-yl)-1,4-dimethylpyridine fumarate Sodium borohydride (300 mg, 8.0 mmol) was added to a solution of (G) (1.6 mmol) and ethanol (15 ml) in a 50 ml flask under nitrogen. The reaction was allowed to stir overnight at room temperature. The reaction was concentrated on the rotary evaporator. Dissolved the resulting solid in 1N $HCl_{(aq)}$ (75 ml), then washing with diethyl ether. The aqueous layer was basified, then extracted with methylene chloride (4×75 ml). The combined organic extracts were dried over $NaCl/Na_2SO_4$, and concentrated to yield an oil which was purified by flash chromatography (silica gel eluting with $NH_4OH$/ethanol in chloroform). Yield was 91 mg. Isolated as fumarate salt, 130.4 mg m.p. 99°–105° C. Analysis calc. for $C_{14}H_{19}N_3O_5S$.C: 49.26; H: 5.61; N: 12.31. Found C: 49.11; H: 5.53; N: 12.03. Compound 1.

EXAMPLE 2

The following compound was made in exactly the same manner as described in example 1F through H using hexanol instead of methanol. 3-(4-Hexyloxy-1,2,5-thiadiazol-3-yl)-1,2,5,6-tetrahydrohydro-1,4-dimethylpyridine oxalate, m.p. 109°–111° C. Analysis calc. for $C_{17}H_{27}N_3O_5S$. C: 52.97; H: 7.06; N: 10.70. Found C: 53.17; H: 6.88; N: 10.98. Compound 2.

EXAMPLE 3

A.
Alpha-amino-alpha-(6-methyl-3-pyridinyl)acetonitrile

To a solution of potassium cyanide (6.96 g, 107 mmol) and ammonium chloride (5.72 g, 107 mmol) in water (5 ml) was added 6-methyl-3-pyridin-carboxaldehyde (8.68 g, 71.5 mmol) and the reaction mixture was stirred at room temperature for 18 h. The reaction mixture was basified with 50% NaOH and extracted with ethyl acetate. The organic phase was dried ($MgSO_4$) and evaporated to give the crude desired product in 7 g yield. The product was used without further purification.

B.
3-(3-Chloro-1,2,5-thiadiazol-4-yl)-6-methylpyridine

A solution of sulphurmonochloride (11.7 ml, 142 mmol) in DMF (50 ml) was slowly added to a solution of alpha-amino-alpha-(6-methyl-3-pyridinyl)acetonitrile (7 g, 47 mmol) at room temperature. The reaction mixture was stirred for 18 h and thereafter basified with 50% NaOH and extracted with ether. The ether phases were dried ($MgSO_4$ and evaporated. The residue was purified by column chromatography (eluent, $EtOAc:CH_2Cl_2$ (1:1)) to give the wanted product in 5.30 g (54%) yield.

C. 3-(3-Hexylthio-1,2,5-thiadiazol-4-yl)-6-methyl pyridine

Sodium hydrogen sulfide monohydrate (0.33 g, 4.4 mmol) was added to a solution of 3-(3-chloro-1,2,5-thiadiazol-4-yl)-6-methylpyridine (0.85 g, 4 mmol) in DMF (20 ml) at room temperature and the reaction mixture was stirred for 1 h. Potassium carbonate (1.65 g, 12 mmol) and 1-hexylbromide (0.99 g, 6 mmol) were added and the reaction mixture was stirred for additionally 24 h. 1N HCl was added and the reaction mixture was extracted once with ether. The aqueous phase was basilled with 50% NaOH and extracted with ether. The ether phases were dried and evaporated to give crude title compound.

D. 3-(3-Hexylthio-1,2,5-thiadiazol-4-yl)-1,6-dimethylpyridinium iodide

Methyl iodide (1 ml, 15 mmol) was added to a solution of 3-(3-hexylthio-1,2,5-thiadiazol-4-yl)-6-methylpyridine (4 mmol) in acetone (5 ml) and the reaction mixture was stirred at room temperature for 20 h. Evaporation of the reaction mixture gave the crude product, which was used without further purification.

E. 3-(3-Hexylthio-1,2,5-thiadiazol-4-yl)-1,2,5,6-tetrahydro-1,6-dimethylpyridine oxalate Under nitrogen sodium borohydride (380 mg, 10 mmol) was added to a solution of 3-(3-hexylthio-1,2,5-thiadiazol-4-yl)-1,6-dimethylpyridinium iodide (4 mmol) in ethanol (99.9%, 20 ml) at −10° C. The reaction mixture was stirred at −10° C. for 1 h. After evaporation the residue was dissolved in water and extracted with ethyl acetate. The dried organic phases were evaporated and the residue purified by column chromatography (eluent: EtOAc:MeOH (4:1)). The title compound was crystallized as the oxalate salt from acetone. Recrystallization from acetone gave the wanted product in 700 mg yield. M.p. 127°–128° C. (Compound 3).

EXAMPLE 4

The following compounds were made in the same manner as described in example 3C through E using the appropriate alkylbromide instead of 1-hexylbromide:

3-(3-Pentylthio-1,2,5-thiadiazol-4-yl )-1,2,5,6-tetrahydro-1,6-dimethylpyridine oxalate, m.p. 112°–113° C. (Compound 4).

3-(3-(4-Cyanobenzylthio)-1,2,5-thiadiazol-4-yl)-1,2,5,6-tetrahydro-1,6-dimethylpyridine oxalate, m.p. 74°–76° C. (Compound 5).

3-(3-(4-Cyanobutylthio)-1,2,5-thiadiazol-4-yl)-1,2,5,6-tetrahydro-1,6-dimethylpyridine oxalate, m.p. 99°–101° C. (Compound 8).

3-(3-Butylthio-1,2,5-thiadiazol-4-yl)-1,2,5,6-tetrahydro-1, 6-dimethylpyridine oxalate, m.p. 119°–120° C. (Compound 9).

3-( 3-Ethylthio-1,2,5-thiadiazol-4-yl )-1,2,5,6-tetrahydro-1, 6-dimethylpyridine oxalate, m.p. 154°–155° C. ( Compound 13).

3-(3-(4-Pentynylthio)-1,2,5-thiadiazol-4-yl)-1,2,5,6-tetrahydro-1,6-dimethylpyridine oxalate, m.p. 111°–113° C. (Compound 14).

3-(3-(3-Phenylpropylthio)-1,2,5-thiadiazol-4-yl)-1,2,5,6-tetrahydro-1,6-dimethylpyridine oxalate, m.p. 125°–126° C. (Compound 15).

EXAMPLE 5

A.
3-(3-Hexyloxy-1,2,5-thiadiazol-4-yl)-6-methylpyridine

Sodium hydride (0.72 g, 15 mmol) was dissolved in dry THF (20 ml) and 1-hexanol (1.53 g, 15 mmol) and a solution of 3-(3-chloro-1,2,5-thiadiazol-4-yl)-6-methylpyridine (1.06 g, 5 mmol) in dry THF (15 ml) was added. The reaction mixture was stirred for 2 h. After addition of water the mixture was extracted with ether, and the ether phase was dried and evaporated. The residue consisted of the crude title compound, which was used without further purification.

B. 3-(3-Hexyloxy-1,2,5-thiadiazol-4-yl)-1,2,5,6-tetrahydro-1,6-dimethylpyridine oxalate M.p. 99°–100° C. (Compound 6) was made in the same manner as described in example 3D through 3E.

EXAMPLE 6

The following compounds were prepared in the same manner as described in example 5 using the appropriate alcohol instead of 1-hexanol:

3-(3-Pentyloxy-1,2, 5-thiadiazol-4-yl)-1,2,5,6-tetrahydro-1, 6-dimethylpyridine oxalate, m.p. 122°–123° C. (Compound 7).

3-(3-Butoxy-1,2,5-thiadiazol-4-yl)-1,2,5,6-tetrahydro-1,6-dimethylpyridine oxalate, m.p. 133°–134° C. (Compound 10).

3-(3-(4-Pentenyloxy)-1,2,5-thiadiazol-4-yl)-1,2,5,6-tetrahydro-1,6-dimethylpyridine oxalate, m.p. 133°–134° C. (Compound 11).

3-(3-(3-Hexynyloxy)-1,2,5-thiadiazol-4-yl)-1,2,5,6-tetrahydro-1,6-dimethylpyridine oxalate, m.p. 126°–128° C. (Compound 12).

3-( 3-Ethoxy-1,2, 5-thiadiazol-4-yl )-1,2,5,6-tetrahydro-1,6-dimethylpyridine oxalate, m.p. 128°–129° C. (Compound 16).

We claim:

1. A method for treating glaucoma in a subject in need thereof, comprising administering topically to said subject an effective amount of a compound of formula I

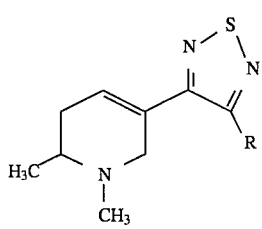

(I)

R is —OR$^5$ or —SR$^5$, wherein R$^5$ is straight or branched C$_{1-15}$-alkyl, straight or branched C$_{2-15}$-alkenyl, straight or branched C$_{2-15}$-alkynyl, or straight or branched C$_{1-15}$-alkyl which is substituted with cyano or a phenyl group wherein the phenyl group is optionally substituted with CN; or a pharmaceutically acceptable salt thereof.

2. The method according to claim 1, wherein R is —OR$^5$, wherein R$^5$ is straight or branched C$_{1-15}$-alkyl.

3. The method according to claim 1, wherein R is —SR$^5$, wherein R$^5$ is straight or branched C$_{1-15}$-alkyl.

4. The method according to claim 1, wherein the compound is selected from the group consisting of:

3-(3-Hexylthio-1,2,5-thiadiazol-4-yl)- 1,2,5,6-tetrahydro-1,6-dimethylpyridine;

3-(3-Pentylthio-1,2,5-thiadiazol-4-yl)- 1,2,5,6-tetrahydro-1,6-dimethylpyridine;

3-( 3-(4-Cyanobenzylthio)-1,2,5-thiadiazol-4- yl)-1,2,5, 6-tetrahydro-1,6-dimethylpyridine;

3-(3-(4-Cyanobutylthio)-1,2,5-thiadiazol-4-yl)-1,2,5,6-tetrahydro-1,6-dimethylpyridine;

3-(3-Butylthio-1,2,5-thiadiazol-4-yl)-1,2,5,6-tetrahydro-1,6-dimethylpyridine;

3-(3-(4-Pentynylthio)-1,2,5-thiadiazol-4-yl)-1,2,5,6-tetrahydro- 1,6-dimethylpyridine;

3-( 3-(3-Phenylpropylthio)-1,2,5-thiadiazol-4-yl)-1,2,5,6-tetrahydro-1,6-dimethylpyridine; and pharmaceutically acceptable salts thereof.

5. The method according to claim 1, wherein the compound is selected from the group consisting of:

3-( 3-Ethylthio-1,2,5-thiadiazol-4-yl)-1,2,5,6-tetrahydro-1,6-dimethylpyridine;

3-(3-Ethoxy-1,2,5-thiadiazol-4-yl)-1,2,5,6-tetrahydro-1, 6-dimethylpyridine; and pharmaceutically acceptable salts thereof.

6. The method according to claim 1, wherein the compound is selected from the group consisting of:

3-(3-Hexyloxy-1,2,5-thiadiazol-4-yl)-1,2,5,6-tetrahydro-1,6-dimethylpyridine;

3-(3-Pentyloxy-1,2,5-thiadiazol-4-yl)-1,2,5,6-tetrahydro-1, 6-dimethylpyridine;

3-( 3-Butoxy-1,2,5-thiadiazol-4-yl)-1,2,5,6-tetrahydro-1,6-dimethylpyridine;

3-(3-(4-Pentenyloxy)-1,2,5-thiadiazol-4-yl)-1,2,5,6-tetrahydro-1,6-dimethylpyridine;

3-(3-(3-Hexynyloxy)-1,2,5-thiadiazol-4-yl)-1,2,5,6-tetrahydro-1,6-dimethylpyridine; and pharmaceutically acceptable salts thereof.

* * * * *